(12) United States Patent
Seo et al.

(10) Patent No.: US 9,829,469 B2
(45) Date of Patent: Nov. 28, 2017

(54) APPARATUS AND METHOD FOR MEASURING NONLINEAR PARAMETERS

(71) Applicant: KOREA RESEARCH INSTITUTE OF STANDARDS AND SCIENCE, Daejeon (KR)

(72) Inventors: Dae Cheol Seo, Daejeon (KR); Seung Hyun Cho, Sejong (KR); Choon Su Park, Daejeon (KR); Seung Seok Lee, Daejeon (KR); Young Min Seong, Busan (KR)

(73) Assignee: Korea Research Institute of Standards and Science (KR)

( * ) Notice: Subject to any disclaimer, the term of this patent is extended or adjusted under 35 U.S.C. 154(b) by 248 days.

(21) Appl. No.: 14/654,647

(22) PCT Filed: Nov. 4, 2013

(86) PCT No.: PCT/KR2013/009889
§ 371 (c)(1),
(2) Date: Jun. 22, 2015

(87) PCT Pub. No.: WO2014/104563
PCT Pub. Date: Jul. 3, 2014

(65) Prior Publication Data
US 2015/0323505 A1    Nov. 12, 2015

(30) Foreign Application Priority Data

Dec. 24, 2012 (KR) .................. 10-2012-0151975
Dec. 24, 2012 (KR) .................. 10-2012-0151976

(51) Int. Cl.
*G01N 29/14* (2006.01)
*G01N 29/24* (2006.01)
*G01N 29/34* (2006.01)

(52) U.S. Cl.
CPC ......... *G01N 29/2418* (2013.01); *G01N 29/14* (2013.01); *G01N 29/343* (2013.01);
(Continued)

(58) Field of Classification Search
CPC .. G01N 29/2418; G01N 29/343; G01N 29/42; G01N 29/11; G01N 29/22; G01N 29/043; G01N 29/221; G01N 29/14
See application file for complete search history.

(56) References Cited

U.S. PATENT DOCUMENTS 5,008,166 A * 4/1991 Aoki ................. G02F 1/133516
257/E31.121
2004/0040379 A1* 3/2004 O'Donnell .......... A61B 5/0095
73/627

(Continued)

FOREIGN PATENT DOCUMENTS

| JP | 2007155730 | 6/2007 |
| KR | 20050022585 A | 3/2005 |
| KR | 20050042542 A | 5/2005 |

OTHER PUBLICATIONS

Hyunjo et al., "Estimation of Fracture Toughness Degradation of High Temperature Materials by Nonlinear Acoustic Effects", Journal of the Korean Society for Nondestrcutive Testing, vol. 20, No. 5, 2000, pp. 424-431.

(Continued)

*Primary Examiner* — Helen Kwok
(74) *Attorney, Agent, or Firm* — Tarolli, Sundheim, Covell & Tummino LLP

(57) ABSTRACT

The present invention relates to a technology for measuring a nonlinear parameter of an object to be measured, and more particularly, to an apparatus and method for measuring a nonlinear parameter of an object to be measured.

20 Claims, 12 Drawing Sheets

(52) U.S. Cl.
CPC ............... *G01N 2291/0258* (2013.01); *G01N 2291/02491* (2013.01); *G01N 2291/101* (2013.01); *G01N 2291/102* (2013.01)

(56) References Cited

U.S. PATENT DOCUMENTS

| | | | |
|---|---|---|---|
| 2005/0023434 A1* | 2/2005 | Yacoubian | G01N 29/2418 250/200 |
| 2005/0072236 A1* | 4/2005 | Heyman | G01N 29/07 73/602 |
| 2007/0125174 A1* | 6/2007 | Ramaswamy | G01N 3/56 73/579 |
| 2008/0022773 A1* | 1/2008 | McKenna | G01H 5/00 73/597 |
| 2014/0316719 A1* | 10/2014 | Lanza di Scalea | G01M 5/0025 702/42 |
| 2015/0241395 A1* | 8/2015 | Kang | G01N 29/2418 73/643 |

OTHER PUBLICATIONS

International Search Report for PCT/KR2013/009889, dated Mar. 3, 2014, pp. 1-3.

* cited by examiner

[Fig. 2]
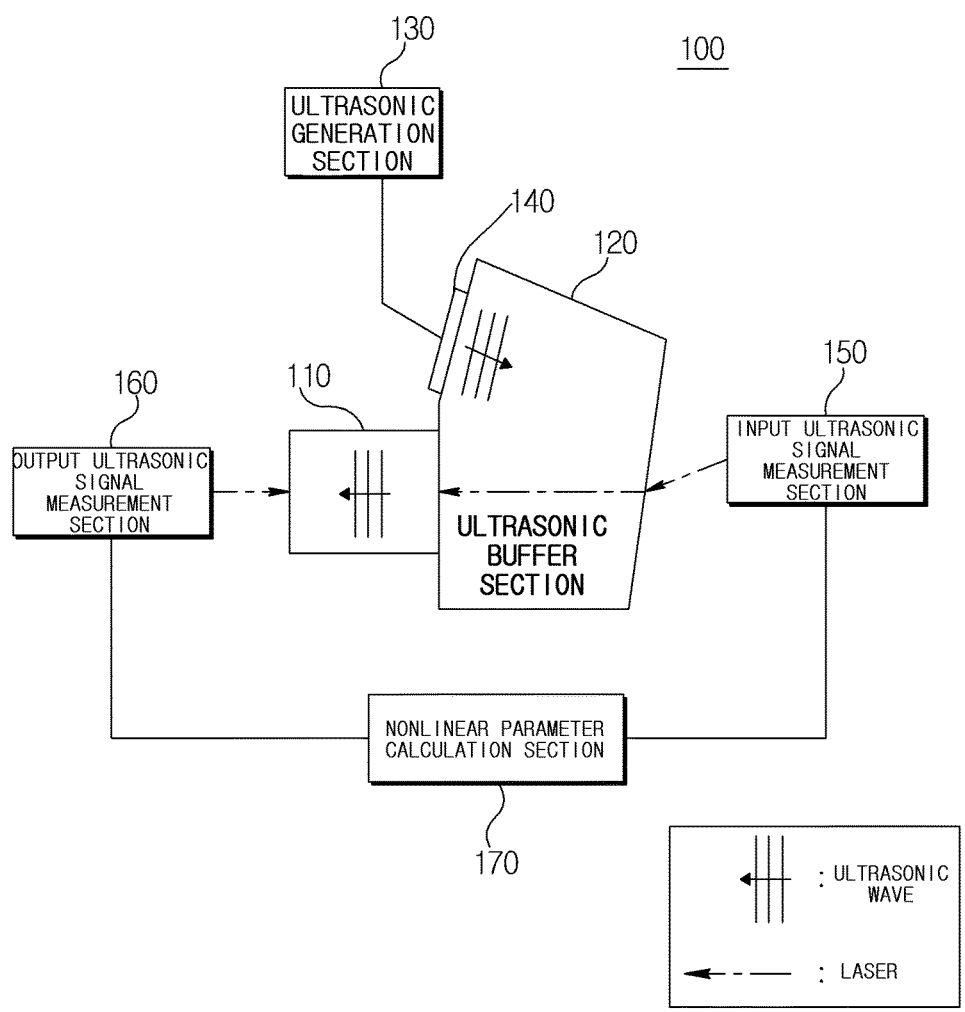

[Fig. 3]
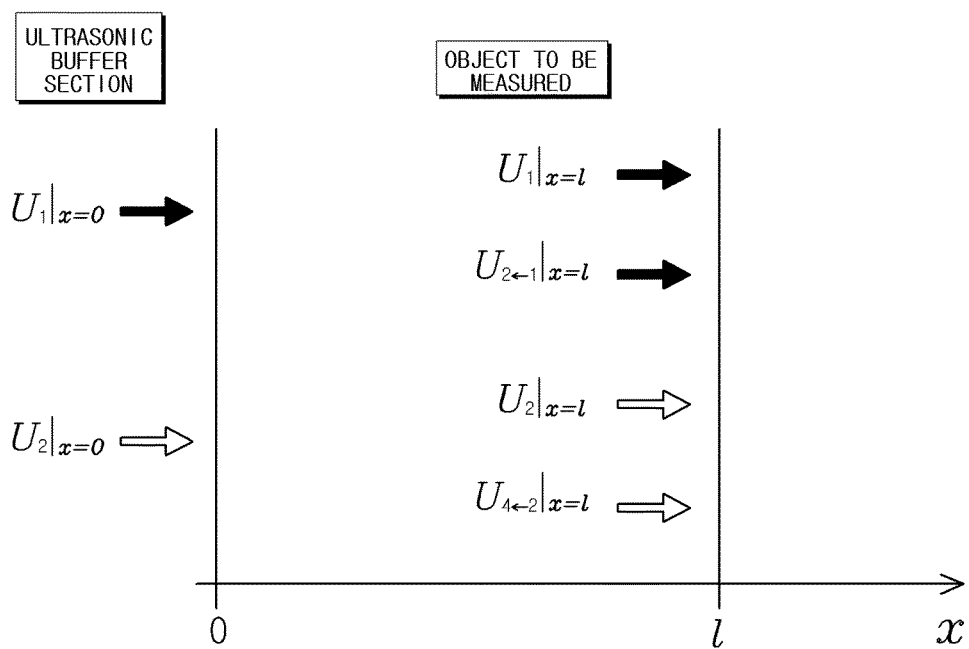

[Fig. 4]
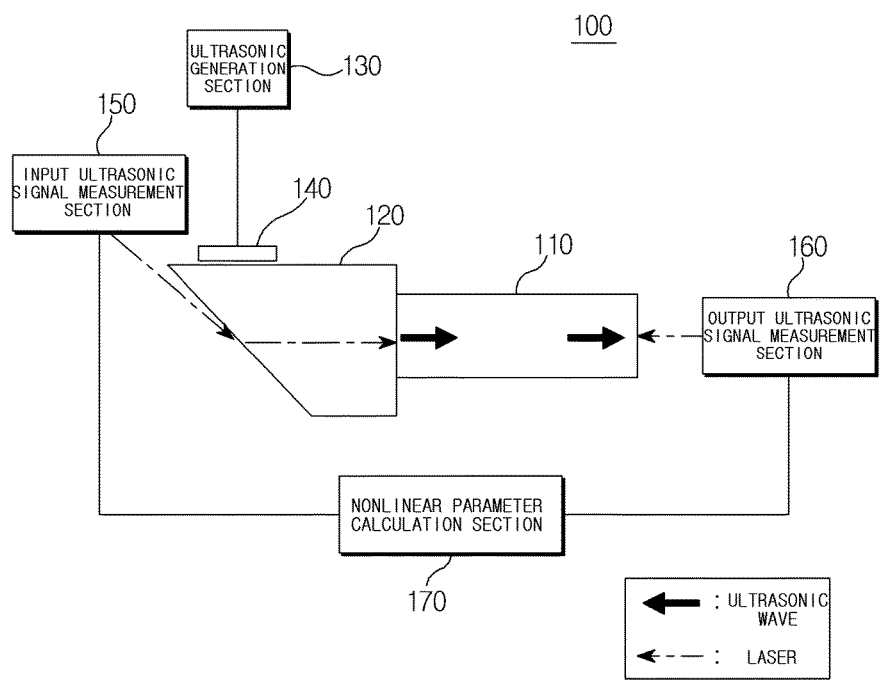

[Fig. 5]
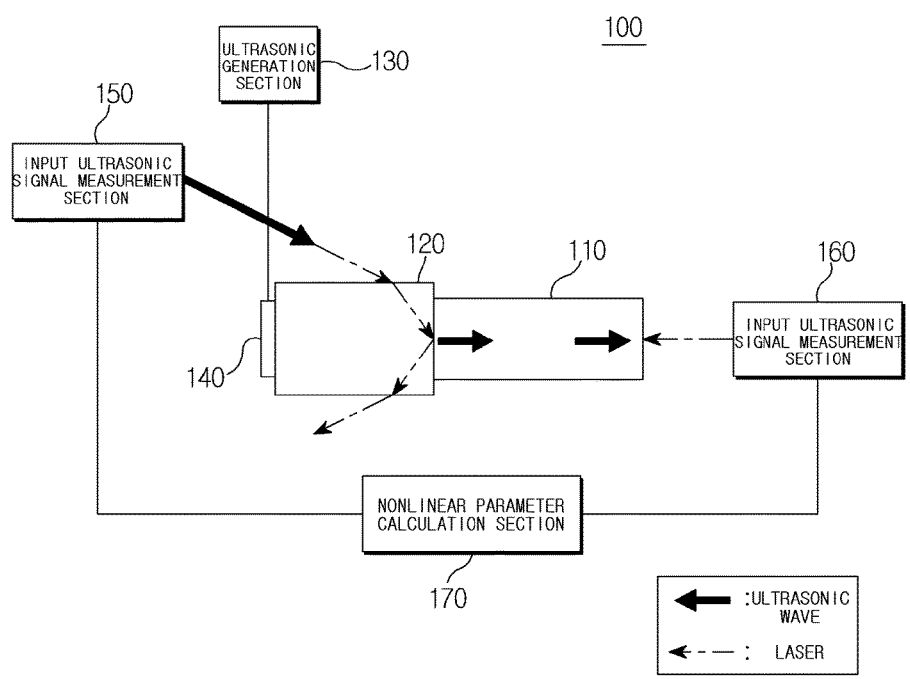

[Fig. 6A]
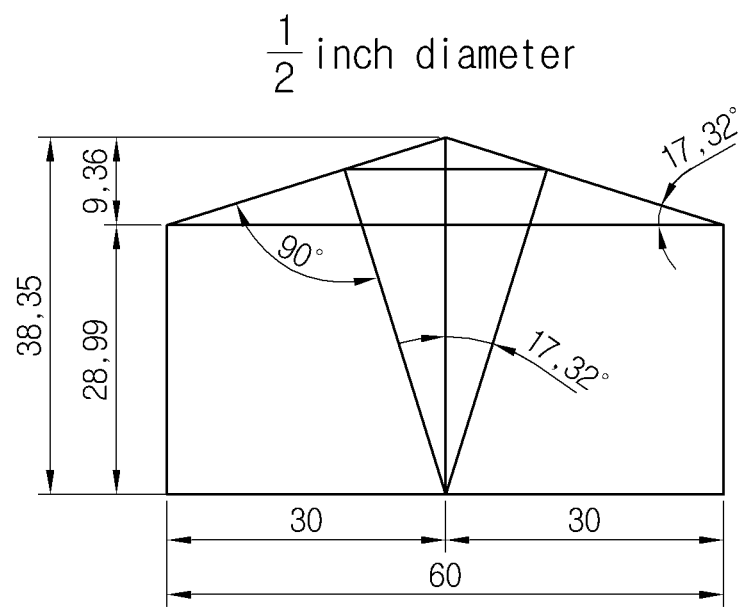

[Fig. 6B]
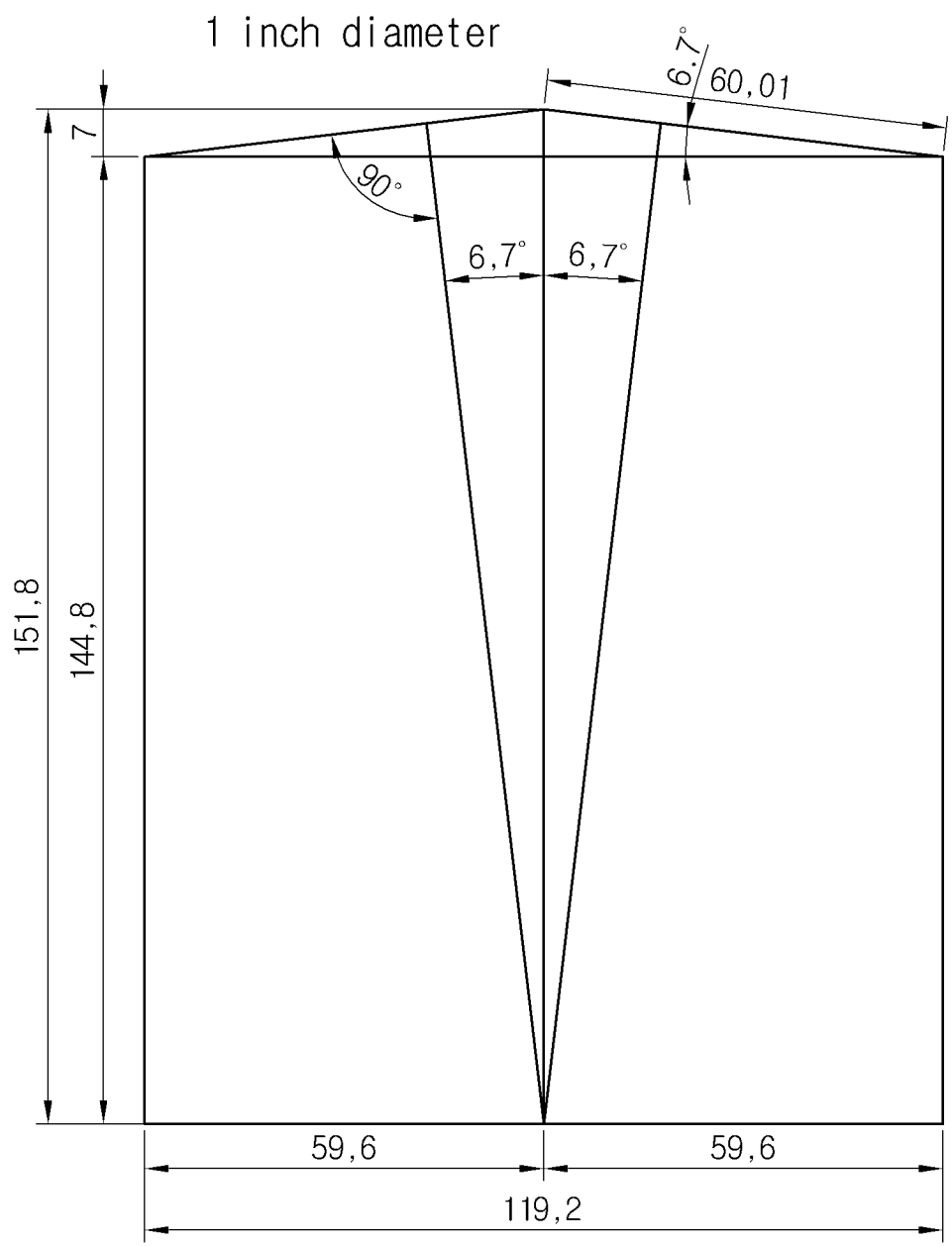

[Fig. 7]
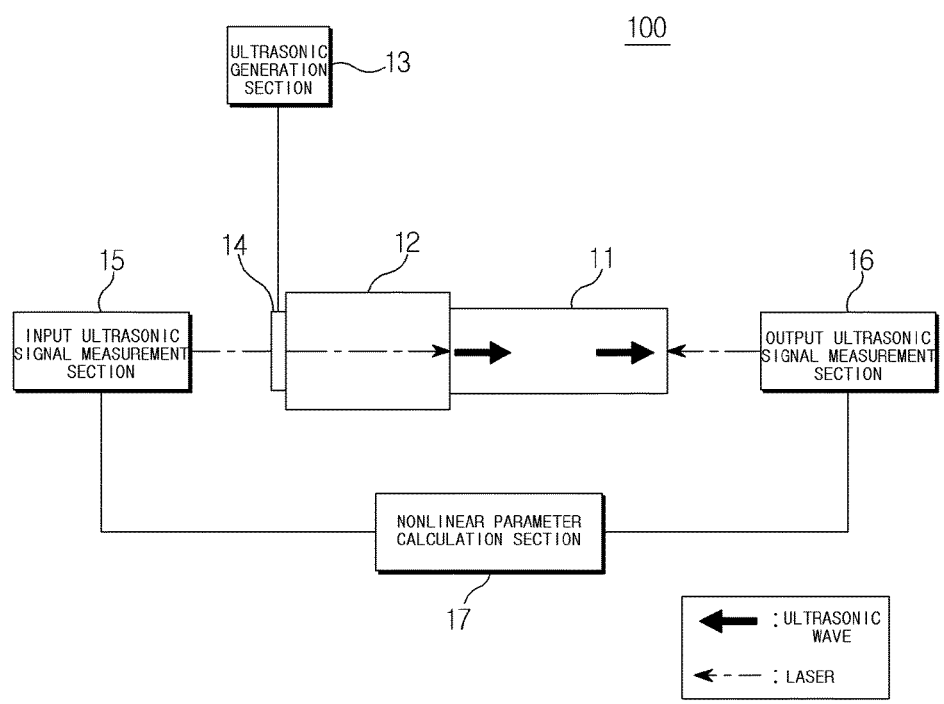

[Fig. 8]
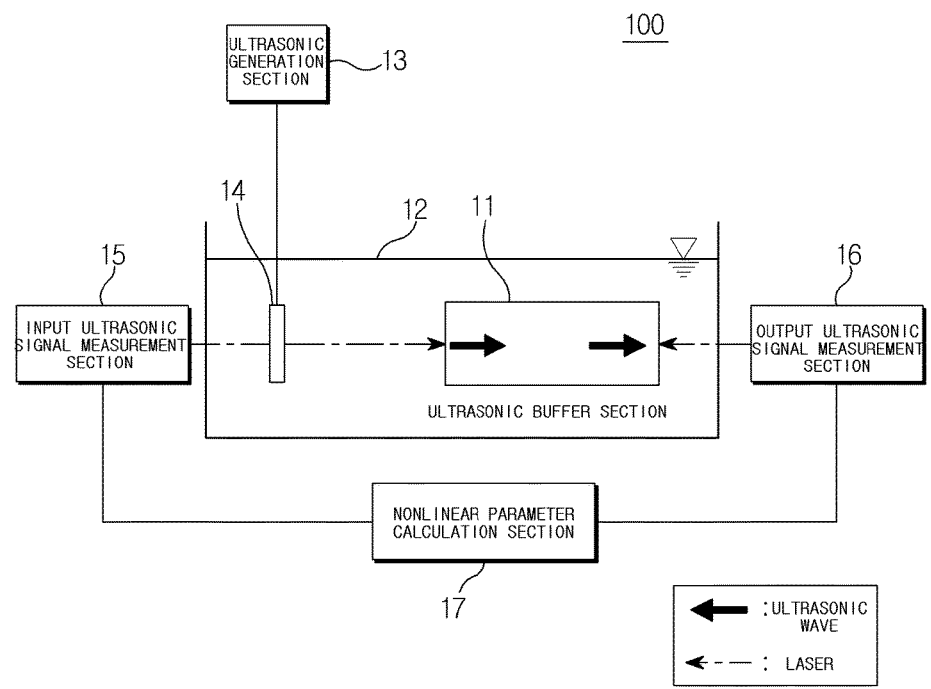

[Fig. 9]
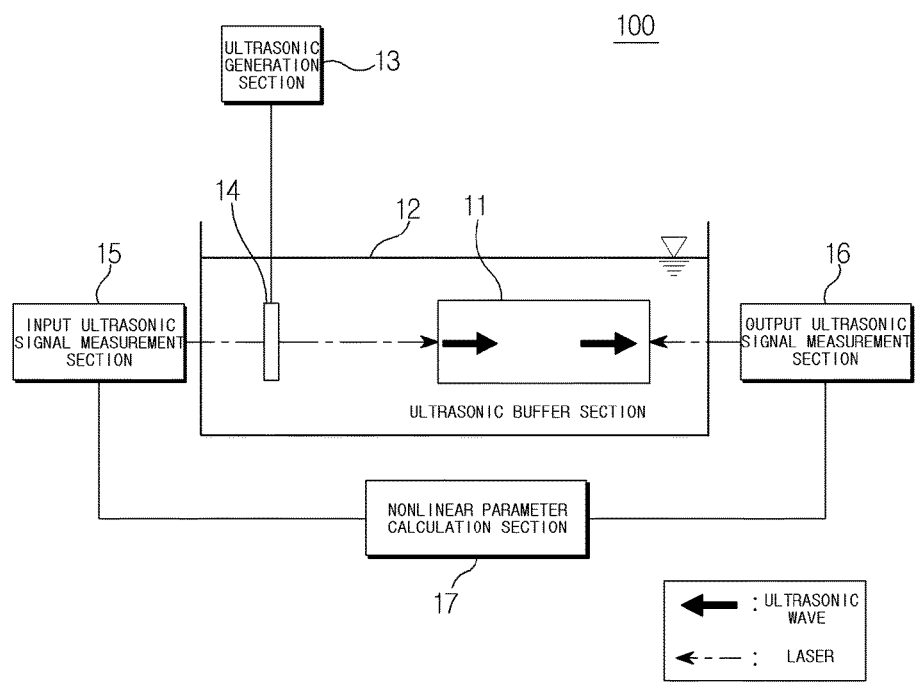

[Fig. 10]
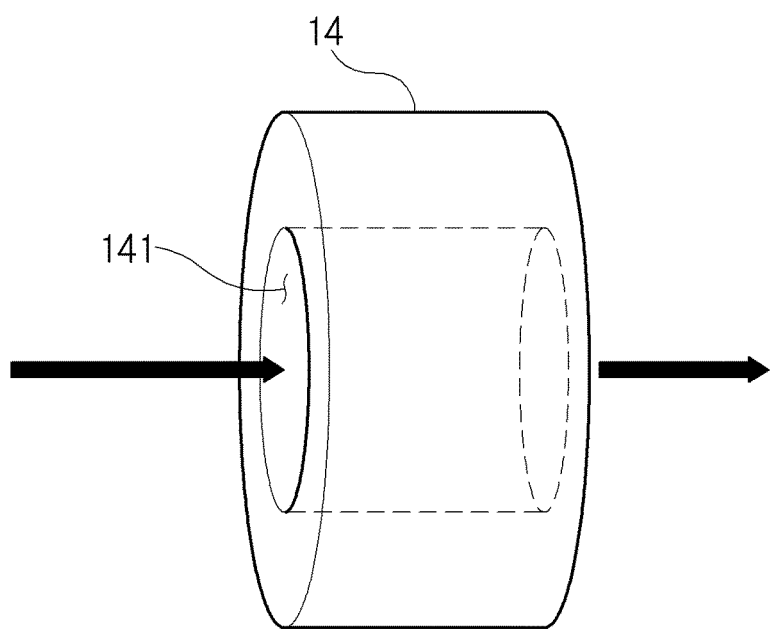
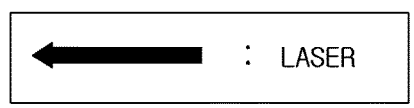 : LASER

[Fig. 11]
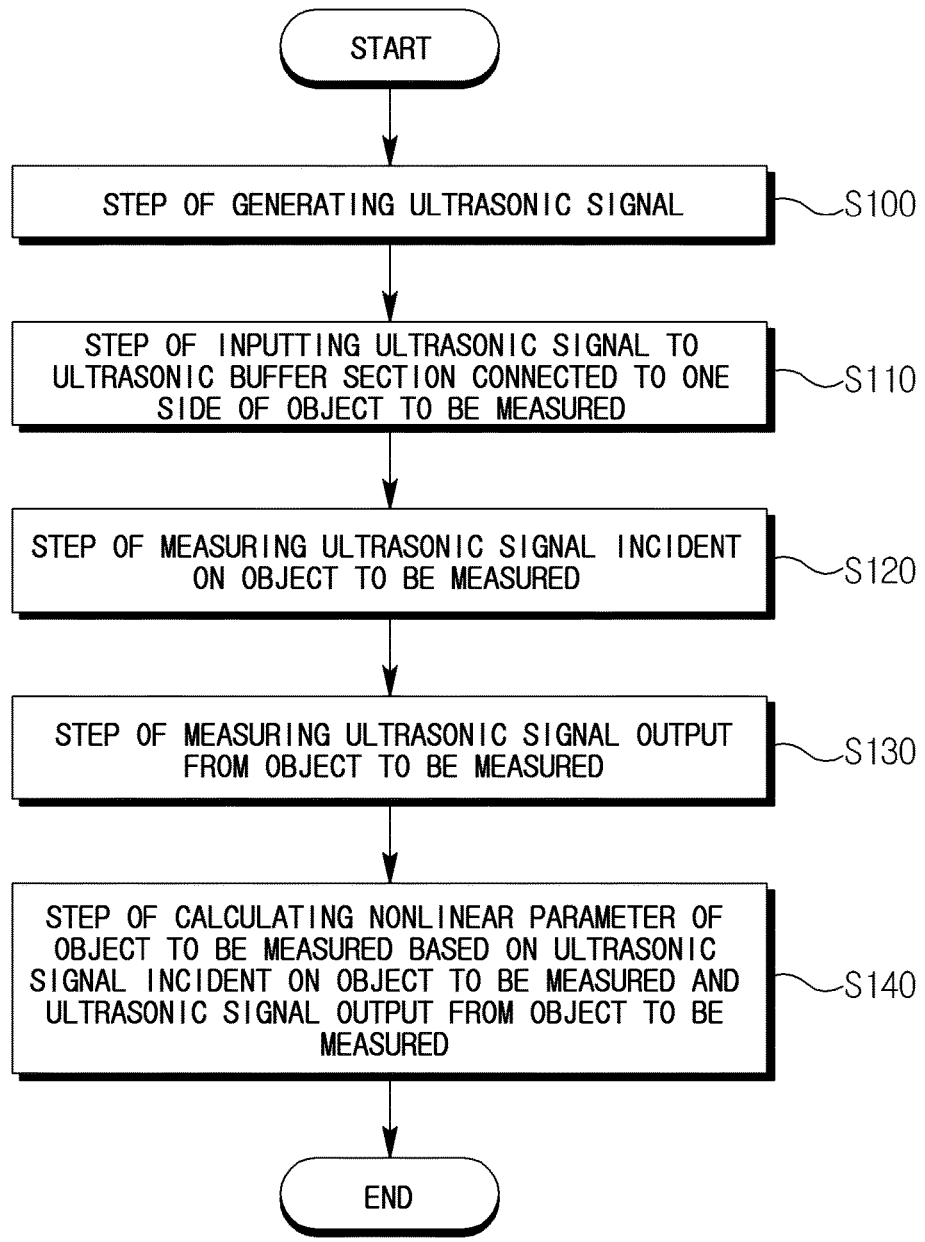

APPARATUS AND METHOD FOR MEASURING NONLINEAR PARAMETERS

RELATED APPLICATIONS

The present invention is a U.S. National Stage under 35 USC 371 patent application, claiming priority to Serial No. PCT/KR2013/009889, filed on 4 Nov. 2013; which claims priority from KR 10-2012-0151975, filed 24 Dec. 2012 and KR10-2012-0151976, filed 24 Dec. 2012, the entirety of which are incorporated herein by reference.

TECHNICAL FIELD

The present invention relates to a technology for measuring a nonlinear parameter of an object to be measured, and more particularly, to an apparatus and method for measuring a nonlinear parameter of an object to be measured.

BACKGROUND ART

Nonlinear parameters of objects to be measured such as materials, specimens, samples and bodies may be measured using ultrasonic waves, having single frequencies, which are a kind of elastic wave. This measurement uses nonlinear behavior of elastic waves, and micro-structural transmutation of objects to be measured caused by degradation such as corrosion and fatigue may be evaluated using nonlinear properties of the elastic waves.

Specifically, a harmonic component is generated in addition to a basic frequency component by nonlinear properties of elastic waves while the elastic waves having single frequencies are propagated through an object to be measured.

A nonlinear parameter of an object to be measured may be measured using the nonlinear properties of elastic waves by measuring sizes of a basic frequency component and a secondary harmonic component of a signal propagated to the object and by calculating a relative ratio between the sizes of the basic frequency component and the secondary harmonic component. The relative ratio is typically defined as a nonlinear parameter β and is expressed by the following Equation 1.

$$\beta = \frac{8}{xk^2} \frac{A_2}{A_1^2} \quad \text{[Equation 1]}$$

Here, $A_1$ and $A_2$ are amplitudes of the primary (basic) frequency component and the secondary harmonic component, respectively, k is a wave number, and x is a propagation distance. In addition, the primary frequency component means an ultrasonic signal having the same frequency as the basic frequency component, and the secondary harmonic component means a high-frequency ultrasonic signal having a frequency twice the basic frequency.

FIG. 1A is a conceptual diagram for explaining a method of measuring a nonlinear parameter of an object to be measured according to the related art. FIG. 1B is a graph illustrating an ultrasonic signal output from the object to be measured according to the related art.

Referring to FIGS. 1A and 1B, when an ultrasonic signal having a single frequency component is incident on an object to be measured 20 through a probe 10, an ultrasonic signal having a secondary harmonic component of the single frequency component is output as an ultrasonic wave to be detected by a probe 30, in addition to the ultrasonic signal having the single frequency component, due to degradation generated inside the object to be measured 20.

In the signal detected by the probe, a basic frequency component having an amplitude of $A_1$ and a frequency of $f_0$, and a secondary harmonic component having an amplitude of $A_2$ and a frequency of $2f_0$ are detected. Accordingly, a nonlinear parameter β may be calculated using the above Equation 1, and a degradation degree of the object to be measured may be evaluated by measuring and comparing nonlinear parameters before and after the generation of degradation.

The nonlinear parameter β has to be measured with consideration for only a harmonic component generated by an object to be measured. However, since harmonic components generated by electrical systems including the probe as well as the harmonic component generated by the object to be measured may be considered when the nonlinear parameter is actually measured, it is difficult to accurately measure the nonlinear parameter.

For example, when the probe is a contact probe coming into contact with an object to be measured, an unnecessary wavelength may be generated due to an irregular contact pressure between the probe and the object to be measured and thus a nonlinear component may be generated. For this reason, it is difficult to accurately the nonlinear parameter of the object to be measured.

Therefore, nonlinearity of the object to be measured may not be accurately measured due to addition of the nonlinear component generated by the above problems, besides the nonlinear parameter of the object to be measured.

DISCLOSURE

Technical Problem

Accordingly, the present invention has been made in view of the above-mentioned problems, and an object thereof is to provide a nonlinear parameter measurement apparatus capable of accurately measuring a nonlinear parameter of an object to be measured.

In addition, another object of the present invention is to provide a nonlinear parameter measurement method capable of accurately measuring a nonlinear parameter of an object to be measured.

Technical Solution

In accordance with an aspect of the present invention, a nonlinear parameter measurement apparatus for measuring a nonlinear parameter of an object to be measured using an ultrasonic signal, the nonlinear parameter measurement apparatus includes an ultrasonic buffer section connected to one side of the object to be measured to input an ultrasonic signal to the object to be measured, an ultrasonic generation section generating the ultrasonic signal by generation of a tone-bust, a probe connected to the ultrasonic buffer section such that the ultrasonic signal generated by the ultrasonic generation section is incident on the ultrasonic buffer section, an input ultrasonic signal measurement section measuring the ultrasonic signal incident on the object to be measured by irradiating the ultrasonic buffer section with laser, an output ultrasonic signal measurement section measuring an ultrasonic signal output from the object to be measured by irradiating the other side of the object to be measured with laser, and a nonlinear parameter calculation section calculating the nonlinear parameter of the object to be measured, based on the ultrasonic signals measured by the input ultrasonic signal measurement section and the output ultrasonic signal measurement section.

The ultrasonic signal may be incident as a plane wave on the object to be measured by the ultrasonic buffer section, and the ultrasonic buffer section may transmit the laser emitted from the input ultrasonic signal measurement section.

The ultrasonic signal and the laser emitted from the input ultrasonic signal measurement section may be vertically incident on an incident surface of the object to be measured by the ultrasonic buffer section.

The ultrasonic signal and the laser emitted from the input ultrasonic signal measurement section may be obliquely incident on an incident surface of the object to be measured by the ultrasonic buffer section.

The ultrasonic signal incident on the object to be measured may include a basic frequency component and an incident harmonic component of the ultrasonic signal.

The input ultrasonic signal measurement section may measure the ultrasonic signal incident on the object to be measured by measuring a displacement on a surface of the object to be measured on which the ultrasonic signal is incident by means of laser.

The ultrasonic signal output from the object to be measured may include a basic frequency component of the ultrasonic signal output from the object to be measured, a secondary harmonic component relative to the basic frequency component, an incident harmonic component of the ultrasonic signal, and a secondary harmonic component relative to the incident harmonic component.

The output ultrasonic signal measurement section may measure the ultrasonic signal output from the object to be measured by measuring a displacement on a surface of the object to be measured from which the ultrasonic signal is output by means of laser.

The nonlinear parameter calculation section may calculate the nonlinear parameter of the object to be measured with consideration for an incident harmonic component of the ultrasonic signal which is measured by the input ultrasonic signal measurement section and is incident on the object to be measured.

The probe may have a through-hole, and the through-hole may have a central axis coinciding with a beam axis of the ultrasonic signal.

In accordance with another aspect of the present invention, there is provided an ultrasonic probe for measuring a nonlinear parameter of an object to be measured using an ultrasonic signal, wherein one end of the probe is connected to the object to be measured such that the ultrasonic signal is incident on the object to be measured and the probe has a through-hole therein such that laser incident on the other end of the probe passes through the through-hole.

The through-hole may have a central axis coinciding with a beam axis of the ultrasonic signal.

In accordance with a further aspect of the present invention, a nonlinear parameter measurement method for measuring a nonlinear parameter of an object to be measured using an ultrasonic signal, the nonlinear parameter measurement method includes (a) generating an ultrasonic signal by generation of a tone-bust, (b) inputting the ultrasonic signal to an ultrasonic buffer section connected to one side of the object to be measured, (c) measuring the ultrasonic signal incident on the object to be measured by irradiating the ultrasonic buffer section with laser, (d) measuring an ultrasonic signal output from the object to be measured by irradiating the other side of the object to be measured with laser, and (e) calculating the nonlinear parameter of the object to be measured, based on the measured ultrasonic signal incident on the object to be measured and the measured ultrasonic signal output from the object to be measured.

The ultrasonic signal incident on the object to be measured may be incident as a plane wave.

The ultrasonic signal and the laser may be vertically incident on an incident surface of the object to be measured.

The ultrasonic signal incident on the object to be measured may include a basic frequency component and an incident harmonic component of the ultrasonic signal.

In the above (c), the ultrasonic signal incident on the object to be measured may be measured by measuring a displacement on a surface of the object to be measured on which the ultrasonic signal is incident by means of laser.

The ultrasonic signal output from the object to be measured may include a basic frequency component of the ultrasonic signal, a secondary harmonic component relative to the basic frequency component, an incident harmonic component of the ultrasonic signal, and a secondary harmonic component relative to the incident harmonic component.

In the above (d), the ultrasonic signal output from the object to be measured may be measured by measuring a displacement on a surface of the object to be measured from which the ultrasonic signal is output by means of laser.

In the above (e), the nonlinear parameter of the object to be measured may be calculated with consideration for an incident harmonic component of the ultrasonic signal incident on the object to be measured.

Advantageous Effects

In accordance with the present invention, since a nonlinear parameter of an object to be measured is calculated by irradiating an ultrasonic buffer section with laser to measure an ultrasonic signal incident on the object to be measured and irradiating the other side of the object to be measured with laser to measure an ultrasonic signal output from the object to be measured, the nonlinear parameter can be accurately measured.

Specifically, a harmonic component, which is generated by an electrical system including a probe used to measure the nonlinear parameter to be input to the object to be measured, is measured and considered to calculate the nonlinear parameter. Thus, since only the harmonic component generated by degradation of the object to be measured is considered to calculate the nonlinear parameter, the nonlinear parameter can be accurately measured.

In addition, since the ultrasonic signal input to or output from the object to be measured is measured using laser, it is possible to reduce an unnecessary wavelength generated due to an irregular contact pressure between a contact probe and the object to be measured.

Additional advantages, objects, and features of the invention will be set forth in part in the description which follows and in part will become apparent to those having ordinary skill in the art upon examination of the following or may be learned from practice of the invention.

BRIEF DESCRIPTION OF DRAWINGS

The above and other objects, features and other advantages of the present invention will be more clearly understood from the following detailed description taken in conjunction with the accompanying drawings, in which:

FIG. 2 is a block diagram illustrating a configuration of a nonlinear parameter measurement apparatus according to an embodiment of the present invention;

FIG. 3 is a conceptual diagram for explaining a method of measuring a nonlinear parameter according to the embodiment of the present invention;

FIG. 4 is a block diagram illustrating a configuration of a nonlinear parameter measurement apparatus according to another embodiment of the present invention;

FIG. 5 is a block diagram illustrating a configuration of a nonlinear parameter measurement apparatus according to a still another embodiment of the present invention;

FIGS. 6A and 6B are views illustrating a configuration of an ultrasonic buffer section of the nonlinear parameter measurement apparatus according to the present invention;

FIGS. 7 to 9 are block diagrams illustrating a configuration of a nonlinear parameter measurement apparatus according to a further embodiment of the present invention;

FIG. 10 is a perspective view illustrating a probe for measuring the nonlinear parameter according to the embodiment of the present invention; and FIG. 11 is a flowchart illustrating a nonlinear parameter measurement method according to an embodiment of the present invention.

BEST MODE FOR INVENTION

Figure 1A:
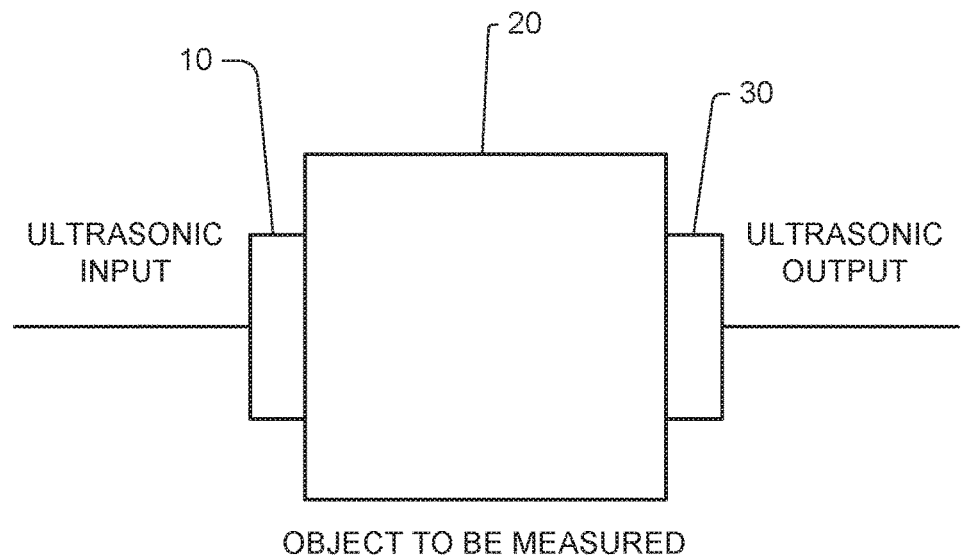
FIG. 1A is a conceptual diagram for explaining a method of measuring a nonlinear parameter of an object to be measured according to the related art.
Figure 1B:
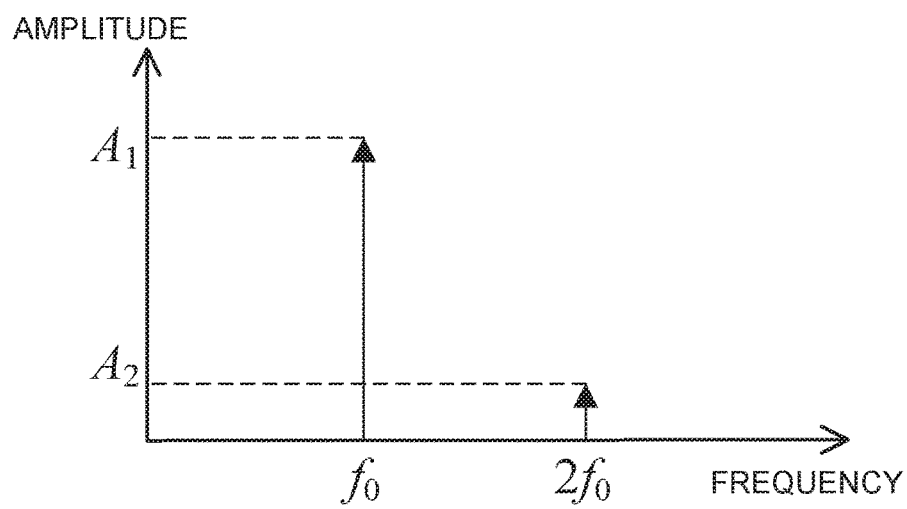
FIG. 1B is a graph illustrating an ultrasonic signal output from the object to be measured according to the related art.

Since various variations may be performed on the exemplary embodiments according to the concept of the present invention and the embodiments of the present invention can be realized in a wide range of varied forms, specific exemplary embodiments of the present invention will be described herein in detail with reference to the appended drawings of the exemplary embodiments of the present invention. However, the present invention will not be limited only to the specific exemplary embodiments of the present invention which are disclosed herein. Therefore, it should be understood that the scope and spirit of the present invention can be extended to all variations, equivalents, and replacements in addition to the appended drawings of the present invention. Throughout the disclosure, like reference numerals refer to like parts throughout the various figures and embodiments of the present invention.

The terms including expressions, such as first, second, A, and/or B, used in the specification of the present invention may be used to describe various elements of the present invention. However, the elements of the present invention should not be limited by the terms used in the specification of the present invention.

In other words, such terms will be used only to differentiate one element from other elements of the present invention. For example, without deviating from the scope and spirit of the present invention, a first element may be referred to as a second element, and, similarly, a second element may also be referred to as a first element. As used herein, the term "and/or" includes any and all combinations of one or more of the associated listed items.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present.

The terminology used in the specification of the present invention is for the purpose of describing particular embodiments only and is not intended to limit the invention. As used in the specification and the appended claims, the singular forms "a", "an" and "the" are intended to include the plural forms as well, unless context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms, including technical and scientific terms, used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Hereinafter, exemplary embodiment of the present invention will be described below in more detail with reference to the accompanying drawings.

FIG. 2 is a block diagram illustrating a configuration of a nonlinear parameter measurement apparatus according to an embodiment of the present invention Referring to FIG. 2, the nonlinear parameter measurement apparatus, which is designated by reference numeral 100, may accurately measure a nonlinear parameter by inputting an ultrasonic signal having a single frequency to an object to be measured 110, detecting an ultrasonic signal output through the object to be measured 110, and calculating the nonlinear parameter with consideration for all of the ultrasonic signals input to and output from the object to be measured 110. The nonlinear parameter measurement apparatus 100 includes an ultrasonic buffer section 120, an ultrasonic generation section 130, a probe 140, an input ultrasonic signal measurement section 150, an output ultrasonic signal measurement section 160, and a nonlinear parameter calculation section 170.

The ultrasonic buffer section 120 may be connected to one side of the object to be measured 110 to input an ultrasonic signal to the object to be measured 110. In addition, the ultrasonic buffer section 120 may input the ultrasonic signal as a plane wave to the object to be measured 110, and may transmit and/or reflect laser emitted from the input ultrasonic signal measurement section 150 to be described later.

In addition, the ultrasonic buffer section 120 may vertically input the ultrasonic signal and the laser emitted from the input ultrasonic signal measurement section 150 to an incident surface of the object to be measured 110.

In addition, the ultrasonic buffer section 120 may be made of a material for transmission and/or reflection of ultrasonic signals and laser. Specifically, the ultrasonic buffer section 120 may be made of transparent plastic, glass, or transparent liquid (for instance, water), but the present invention is not limited thereto.

The ultrasonic generation section 130 may generate the ultrasonic signal by generating a high power tone-burst.

The probe 140 may be connected to the ultrasonic buffer section 120 and the ultrasonic generation section 130 so as to input the ultrasonic signal generated by the ultrasonic generation section 130 to the ultrasonic buffer section 120.

The input ultrasonic signal measurement section 150 may irradiate the ultrasonic buffer section 120 with laser so as to measure an ultrasonic signal incident on the object to be measured 110. Specifically, the input ultrasonic signal measurement section 150 may measure the ultrasonic signal incident on the object to be measured 110 by measuring a displacement on the surface of the object to be measured 110 on which the ultrasonic signal passing through the ultrasonic buffer section 120 is incident by means of laser.

Here, the ultrasonic signal incident on the object to be measured 110 may include a basic frequency component and an incident harmonic component of the ultrasonic signal. The incident harmonic component may be harmonic components generated by an electrical system including a probe, as an ultrasonic wave having a harmonic component in addition to the basic frequency component, and may mean a harmonic component incident on the object to be measured.

For example, when the probe is a contact probe coming into contact with an object to be measured, an unnecessary wavelength may be generated due to an irregular contact pressure between the probe and the object to be measured and be input to the object to be measured. In this case, the unnecessary wavelength is the above incident harmonic component.

The output ultrasonic signal measurement section 160 may irradiate the other side of the object to be measured 110 with laser so as to measure an ultrasonic signal output from the object to be measured 110. Specifically, the output ultrasonic signal measurement section 160 may accurately measure the ultrasonic signal output from the object to be measured 110 by measuring a displacement on the surface of the object to be measured 110 from which the ultrasonic signal is output by means of laser.

Here, the ultrasonic signal output from the object to be measured 110 may include a basic frequency component of the ultrasonic signal output from the object to be measured 110, a secondary harmonic component relative to the basic frequency component, an incident harmonic component of the ultrasonic signal, and a secondary harmonic component relative to the incident harmonic component.

The nonlinear parameter calculation section 170 may calculate a nonlinear parameter of the object to be measured 110, based on the ultrasonic signals measured by the input ultrasonic signal measurement section 150 and the output ultrasonic signal measurement section 160.

Here, the nonlinear parameter calculation section 170 may calculate the nonlinear parameter of the object to be measured 110 with consideration for the incident harmonic component of the ultrasonic signal which is measured by the input ultrasonic signal measurement section 150 and is incident on the object to be measured 110.

Hereinafter, a method in which the nonlinear parameter calculation section 170 calculates the nonlinear parameter with consideration for the incident harmonic component of the ultrasonic signal incident on the object to be measured 110 will be described in detail.

A nonlinear sound wave equation considering attenuation may be expressed by the following Equation 2.

$$\frac{\partial^2 U}{\partial t^2} = c_l^2 \frac{\partial^2 U}{\partial x^2} + \beta \frac{\partial^2 U}{\partial x^2} \frac{\partial U}{\partial x} + \chi \frac{\partial^3 U}{\partial t \partial x^2}$$ [Equation 2]

In Equation 2, $$\frac{\partial^2 U}{\partial t^2} = c_l^2 \frac{\partial^2 U}{\partial x^2}$$

refers to a linear sound wave equation, $$\beta \frac{\partial^2 U}{\partial x^2} \frac{\partial U}{\partial x}$$

is a nonlinear component, and $$\chi \frac{\partial^3 U}{\partial t \partial x^2}$$

is an attenuation component. In addition. U means a wave amplitude function at a time t and a position x.

In order to calculate the nonlinear parameter with consideration for the incident harmonic component of the ultrasonic signal incident on the object to be measured 110, the wave amplitude function U(x, t) is assumed to be a sum of $U_1$ and $U_2$ as indicated by the following Equation 3.

$$U(x,t) = U_1 + U_2 = U_1 e^{-\alpha_1 x} e^{-j(\omega t - kx)} + U_2 e^{-\alpha_2 x} e^{-j2(\omega t - kx)}$$ [Equation 3]

Here, U(x, t) means a wave amplitude function U(x, t) at a time t and a position x, and $U_1$ is a signal in which the basic frequency component of the ultrasonic signal input to the object to be measured 110 passes through the object to be measured 110 and is output from the object to be measured 110. The signal $U_1$ may include a basic frequency component of an ultrasonic signal and a secondary harmonic component of the basic frequency component.

In addition, $U_2$ is a signal in which the incident harmonic component of the ultrasonic signal input to the object to be measured 110 passes through the object to be measured 110 and is output from the object to be measured 110. The signal $U_2$ may include an incident harmonic component of an ultrasonic signal and a secondary harmonic component of the incident harmonic component.

Here, the incident harmonic component of the ultrasonic signal may be harmonic components generated by an electrical system including a probe, as an ultrasonic wave having a harmonic component in addition to the basic frequency component, and may mean a harmonic component incident on the object to be measured 110.

MODE FOR INVENTION

FIG. 3 is a conceptual diagram for explaining a method of measuring the nonlinear parameter according to the embodiment of the present invention.

Referring to FIG. 3, the ultrasonic signal input to the object to be measured from the ultrasonic buffer section includes a basic frequency component $U_1|_{x=0}$ and an incident harmonic component $U_2|_{x=0}$.

In addition, in the ultrasonic signal output from the object to be measured, respective harmonic components relative to the basic frequency component and the incident harmonic component of the ultrasonic signal input from the ultrasonic buffer section are output. Specifically, the ultrasonic signal output from the object to be measured may include a basic frequency component $U_1|_{x=1}$ of an ultrasonic signal, a secondary harmonic component $U_{2\leftarrow 1}|_{x=1}$ of the basic frequency component, an incident harmonic component $U_2|_{x=1}$ of an ultrasonic signal, and a secondary harmonic component $U_{4\leftarrow 2}|_{x=1}$ of the incident harmonic component.

Accordingly, the signal output from the object to be measured may be expressed by the following Equation 4.

$$U(l, t) = \qquad \text{[Equation 4]}$$
$$U_1 e^{-\alpha_1 l}\sin\omega t - \frac{\beta}{16\alpha_1}\left[\frac{\omega U_1}{c_l}\right]^2 (e^{-2\alpha_1 l} - e^{-4\alpha_1 l})\cos 2\omega t +$$
$$U_2 e^{-\alpha_2 l}\sin 2\omega t - \frac{\beta}{16\alpha_2}\left[\frac{2\omega U_2}{c_l}\right]^2 (e^{-2\alpha_2 l} - e^{-4\alpha_2 l})\cos 4\omega t$$

Here, $$U(l, t) = U_1 e^{-\alpha_1 l}\sin\omega t - \frac{\beta}{16\alpha_1}\left[\frac{\omega U_1}{c_l}\right]^2 (e^{-2\alpha_1 l} - e^{-4\alpha_1 l})\cos 2\omega t$$

refers to a basic frequency component and a secondary harmonic component of the basic frequency component, and $$U_2 e^{-\alpha_2 l}\sin 2\omega t - \frac{\beta}{16\alpha_2}\left[\frac{2\omega U_2}{c_l}\right]^2 (e^{-2\alpha_2 l} - e^{-4\alpha_2 l})\cos 4\omega t$$

refers to an incident harmonic component of an ultrasonic signal and a secondary harmonic component of the incident harmonic component.

Here, an amplitude of the incident harmonic component of the ultrasonic signal may be expressed by the following Equation 5.

$$A(2\omega) = -\frac{\beta}{16\alpha_1}\left[\frac{\omega U_1}{c_l}\right]^2 (e^{-2\alpha_1 l} - e^{-4\alpha_1 l})\cos 2\omega t + \quad \text{[Equation 5]}$$
$$U_2 e^{-\alpha_2 l}\sin 2\omega t$$

In addition, a size of the incident harmonic component of the ultrasonic signal may be expressed by the following Equation 6.

$$|A(2\omega)| = \qquad \text{[Equation 6]}$$
$$\sqrt{\left[-\frac{\beta}{16\alpha_1}\left(\frac{\omega U_1}{c_l}\right)^2 (e^{-2\alpha_1 l} - e^{-4\alpha_1 l})\right]^2 + (U_2 e^{-\alpha_2 l})^2}$$

In addition, the above Equation 6 may be arranged as the following Equation 7 in order to calculate the nonlinear parameter.

$$|\beta| = \frac{16\alpha_1}{(1 - e^{2\alpha_1 l})}\left(\frac{c_l}{\omega}\right)^2 \frac{\sqrt{|A(2\omega)|^2 - (U_2 e^{-\alpha_2 l})^2}}{|A(\omega)|^4} \quad \text{[Equation 7]}$$

When comparing Equation 7 and Equation 1, the conventional nonlinear parameter in Equation 1 is measured with consideration for only the basic frequency component of the ultrasonic signal incident on the object to be measured. For this reason, since the incident harmonic component which is actually incident on the object to be measured and is generated by the electrical system is not considered and is regarded as a harmonic component generated due to the degradation of the object to be measured, the nonlinear parameter may not be accurately measured.

Meanwhile, since the nonlinear parameter in Equation 7 is measured with consideration for the incident harmonic component $(U_2 e^{-\alpha_3 l})^2$ of the ultrasonic signal, the nonlinear parameter may be more accurately calculated compared to the conventional nonlinear parameter in Equation 1.

FIG. 4 is a block diagram illustrating a configuration of a nonlinear parameter measurement apparatus according to another embodiment of the present invention. FIG. 5 is a block diagram illustrating a configuration of a nonlinear parameter measurement apparatus according to a still another embodiment of the present invention.

Referring to FIGS. 4 and 5, the nonlinear parameter measurement apparatus, which is designated by reference numeral 100, includes an ultrasonic buffer section 120, an ultrasonic generation section 130, a probe 140, an input ultrasonic signal measurement section 150, an output ultrasonic signal measurement section 160, and a nonlinear parameter calculation section 170.

The ultrasonic buffer section 120 may be connected to one side of an object to be measured 110 to input an ultrasonic signal to the object to be measured 110. In addition, the ultrasonic buffer section 120 may input the ultrasonic signal as a plane wave to the object to be measured 110, and may transmit and/or reflect laser emitted from the input ultrasonic signal measurement section 150 to vertically or obliquely input the laser to an incident surface of the object to be measured 110 on which the ultrasonic signal is incident.

In addition, the ultrasonic buffer section 120 may be made of a material for transmission and/or reflection of ultrasonic signals and laser. Specifically, the ultrasonic buffer section 120 may be made of transparent plastic, glass, or transparent liquid (for instance, water), but the present invention is not limited thereto.

Meanwhile, FIGS. 6A and 6B are views illustrating a configuration of the ultrasonic buffer section of the nonlinear parameter measurement apparatus according to the present invention. The ultrasonic buffer section 120 may be configured in various shapes for vertically or obliquely inputting ultrasonic signals and laser to the incident surface of the object to be measured 110, in addition to the shapes illustrated in FIGS. 4 and 5. For example, the ultrasonic buffer section 120 may have a polygonal shape, but the present invention is not limited thereto.

Since the ultrasonic generation section 130, the probe 140, the input ultrasonic signal measurement section 150, the output ultrasonic signal measurement section 160, and the nonlinear parameter calculation section 170 have the same configurations as those in FIG. 2, description thereof will be omitted.

FIGS. 7 to 9 are block diagrams illustrating a configuration of a nonlinear parameter measurement apparatus according to a further embodiment of the present invention.

Referring to FIGS. 7 to 9, the nonlinear parameter measurement apparatus, which is designated by reference numeral 100, may accurately measure a nonlinear parameter by inputting an ultrasonic signal having a single frequency to an object to be measured 11, detecting an ultrasonic signal output through the object to be measured 11, and calculating the nonlinear parameter with consideration for all of the ultrasonic signals input to and output from the object to be measured 11. The nonlinear parameter measurement apparatus 100 includes an ultrasonic buffer section 12, an ultrasonic generation section 13, a probe 14, an input ultrasonic signal measurement section 15, an output ultrasonic signal measurement section 16, and a nonlinear parameter calculation section 17.

The ultrasonic buffer section 12 may be connected to one side of the object to be measured 11 to input an ultrasonic signal to the object to be measured 11. In addition, the ultrasonic buffer section 12 may input the ultrasonic signal as a plane wave to the object to be measured 11, and may transmit and/or reflect laser emitted from the input ultrasonic signal measurement section 15 to be described later.

In addition, the ultrasonic buffer section 12 may vertically input the ultrasonic signal and the laser emitted from the input ultrasonic signal measurement section 15 to an incident surface of the object to be measured 11.

In addition, the ultrasonic buffer section 12 may be made of a material for transmission and/or reflection of ultrasonic signals and laser. Specifically, the ultrasonic buffer section 12 may be made of transparent plastic, glass, or transparent liquid (for instance, water), but the present invention is not limited thereto.

The ultrasonic generation section 13 may generate the ultrasonic signal by generating a high power tone-burst.

The probe 14 may be connected to the ultrasonic buffer section 12 and the ultrasonic generation section 13 so as to input the ultrasonic signal generated by the ultrasonic generation section 13 to the ultrasonic buffer section 12.

In addition, the probe 14 may be connected to the ultrasonic buffer section 12, and may have a through-hole therein. Thus, the ultrasonic signal generated by the ultrasonic generation section 13 may be incident on the ultrasonic buffer section 12.

Here, the through-hole may have a central axis formed to coincide with a beam axis of the ultrasonic signal.

The probe 14 will be described in detail with reference to FIG. 10.

The input ultrasonic signal measurement section 15 may irradiate the ultrasonic buffer section 12 with laser so as to measure an ultrasonic signal incident on the object to be measured 11. Specifically, the input ultrasonic signal measurement section 15 may measure the ultrasonic signal incident on the object to be measured 11 by measuring a displacement on the surface of the object to be measured 11 on which the ultrasonic signal passing through the ultrasonic buffer section 12 is incident by means of laser.

In addition, the input ultrasonic signal measurement section 15 may measure the ultrasonic signal incident on the object to be measured 11 by irradiating the ultrasonic buffer section 12 with laser through the through-hole formed within the probe 14.

Here, the ultrasonic signal incident on the object to be measured 11 may include a basic frequency component and an incident harmonic component of the ultrasonic signal. The incident harmonic component may be harmonic components generated by an electrical system including a probe, as an ultrasonic wave having a harmonic component in addition to the basic frequency component, and may mean a harmonic component incident on the object to be measured.

For example, when the probe is a contact probe coming into contact with an object to be measured, an unnecessary wavelength may be generated due to an irregular contact pressure between the probe and the object to be measured and be input to the object to be measured. In this case, the unnecessary wavelength is the above incident harmonic component.

The output ultrasonic signal measurement section 16 may irradiate the other side of the object to be measured 11 with laser so as to measure an ultrasonic signal output from the object to be measured 11. Specifically, the output ultrasonic signal measurement section 16 may accurately measure the ultrasonic signal output from the object to be measured 11 by measuring a displacement on the surface of the object to be measured 11 from which the ultrasonic signal is output by means of laser.

Here, the ultrasonic signal output from the object to be measured 11 may include a basic frequency component of the ultrasonic signal output from the object to be measured 11, a secondary harmonic component relative to the basic frequency component, an incident harmonic component of the ultrasonic signal, and a secondary harmonic component relative to the incident harmonic component.

The nonlinear parameter calculation section 17 may calculate a nonlinear parameter of the object to be measured 11, based on the ultrasonic signals measured by the input ultrasonic signal measurement section 15 and the output ultrasonic signal measurement section 16.

Here, the nonlinear parameter calculation section 17 may calculate the nonlinear parameter of the object to be measured 11 with consideration for the incident harmonic component of the ultrasonic signal which is measured by the input ultrasonic signal measurement section 15 and is incident on the object to be measured 11.

Meanwhile, since a method in which the nonlinear parameter calculation section 17 calculates the nonlinear parameter with consideration for the incident harmonic component of the ultrasonic signal incident on the object to be measured 11 is described in detail in FIG. 2, description thereof will be omitted.

FIG. 10 is a perspective view illustrating the probe for measuring the nonlinear parameter according to the embodiment of the present invention.

Referring to FIG. 10, one end of the probe 140 may be connected to the ultrasonic buffer section, and the probe 140 may have the through-hole 141 therein. The ultrasonic signal generated by the ultrasonic generation section may be incident on the ultrasonic buffer section by the probe 140.

In addition, the laser input to the other end of the probe 140 from the input ultrasonic signal measurement section may be transferred to the ultrasonic buffer section through the through-hole 141 formed within the probe 140. Here, the central axis of the through-hole 141 may coincide with the beam axis of the ultrasonic signal.

In addition, the probe 140 may have a structure in which laser penetrates or passes through the probe 140. The probe 140 may have a cylindrical shape as illustrated in FIG. 10, but the present invention is not limited thereto.

FIG. 11 is a flowchart illustrating a nonlinear parameter measurement method according to an embodiment of the present invention.

Referring to FIG. 11, the nonlinear parameter measurement method may accurately measure a nonlinear parameter by inputting an ultrasonic signal having a single frequency to an object to be measured, detecting an ultrasonic signal output through the object to be measured, and calculating the nonlinear parameter with consideration for all of the ultrasonic signals input to and output from the object to be measured.

Specifically, in step S100, the ultrasonic signal may be generated by generation of a high power tone-burst.

Next, in step S110, the ultrasonic signal may be incident on an ultrasonic buffer section connected to one side of the object to be measured.

Next, in step S120, the ultrasonic signal incident on the object to be measured may be measured by irradiating the ultrasonic buffer section with laser. Specifically, the ultrasonic signal incident on the object to be measured may be measured by measuring a displacement on the surface of the object to be measured on which the ultrasonic signal is incident by means of laser. Here, the ultrasonic signal and the laser incident on the object to be measured may be vertically incident on the incident surface of the object to be measured.

In addition, the ultrasonic signal incident on the object to be measured may be incident as a plane wave, and may include a basic frequency component and an incident harmonic component of the ultrasonic signal.

Next, in step S130, the ultrasonic signal output from the object to be measured may be measured by irradiating the other side of the object to be measured with laser. Specifically, the ultrasonic signal output from the object to be measured may be measured by measuring a displacement on the surface of the object to be measured from which the ultrasonic signal is output by means of laser. Here, the laser input to the other side of the object to be measured may be vertically incident on the output surface of the object to be measured from which the ultrasonic signal is output.

In addition, the ultrasonic signal output from the object to be measured may include a basic frequency component of the ultrasonic signal, a secondary harmonic component relative to the basic frequency component, an incident harmonic component of the ultrasonic signal, and a secondary harmonic component relative to the incident harmonic component.

Next, in step S140, the nonlinear parameter of the object to be measured may be calculated based on the measured ultrasonic signal incident on the object to be measured and the measured ultrasonic signal output from the object to be measured. That is, the nonlinear parameter of the object to be measured may be calculated with consideration for the incident harmonic component of the ultrasonic signal incident on the object to be measured.

Since the specific method of calculating the nonlinear parameter is described in FIG. 2, description thereof will be omitted.

Although the present invention has been described with respect to the illustrative embodiments, it will be apparent to those skilled in the art that various variations and modifications may be made without departing from the spirit and scope of the invention as defined in the following claims.

INDUSTRIAL APPLICABILITY

The present invention may be applied to an apparatus and method for measuring a nonlinear parameter of an object to be measured.

The invention claimed is:

1. A nonlinear parameter measurement apparatus for measuring a nonlinear parameter of an object to be measured using an ultrasonic signal, the nonlinear parameter measurement apparatus comprising:
an ultrasonic buffer section connected to one side of the object to be measured to input an ultrasonic signal to the object to be measured;
an ultrasonic generation section generating the ultrasonic signal by generation of a tone-bust;
a probe connected to the ultrasonic buffer section such that the ultrasonic signal generated by the ultrasonic generation section is incident on the ultrasonic buffer section;
an input ultrasonic signal measurement section measuring the ultrasonic signal incident on the object to be measured by irradiating the ultrasonic buffer section with a laser;
an output ultrasonic signal measurement section measuring an ultrasonic signal output from the object to be measured by irradiating the other side of the object to be measured with the laser; and
a nonlinear parameter calculation section calculating the nonlinear parameter of the object to be measured, based on the ultrasonic signals measured by the input ultrasonic signal measurement section and the output ultrasonic signal measurement section.

2. The nonlinear parameter measurement apparatus according to claim 1, wherein the ultrasonic signal is incident as a plane wave on the object to be measured by the ultrasonic buffer section, and the ultrasonic buffer section transmits the laser emitted from the input ultrasonic signal measurement section.

3. The nonlinear parameter measurement apparatus according to claim 2, wherein the ultrasonic signal and the laser emitted from the input ultrasonic signal measurement section are vertically incident on an incident surface of the object to be measured by the ultrasonic buffer section.

4. The nonlinear parameter measurement apparatus according to claim 2, wherein the ultrasonic signal and the laser emitted from the input ultrasonic signal measurement section are obliquely incident on an incident surface of the object to be measured by the ultrasonic buffer section.

5. The nonlinear parameter measurement apparatus according to claim 1, wherein the ultrasonic signal incident on the object to be measured comprises a basic frequency component and an incident harmonic component.

6. The nonlinear parameter measurement apparatus according to claim 1, wherein the input ultrasonic signal measurement section measures the ultrasonic signal incident on the object to be measured by measuring a displacement on a surface of the object to be measured on which the ultrasonic signal is incident by the laser.

7. The nonlinear parameter measurement apparatus according to claim 1, wherein the ultrasonic signal output from the object to be measured comprises a basic frequency component of the ultrasonic signal output from the object to be measured, a secondary harmonic component relative to the basic frequency component, an incident harmonic component of the ultrasonic signal, and a secondary harmonic component relative to the incident harmonic component.

8. The nonlinear parameter measurement apparatus according to claim 1, wherein the output ultrasonic signal measurement section measures the ultrasonic signal output from the object to be measured by measuring a displacement on a surface of the object to be measured from which the ultrasonic signal is output by the laser.

9. The nonlinear parameter measurement apparatus according to claim 1, wherein the nonlinear parameter calculation section calculates the nonlinear parameter of the object to be measured with consideration for an incident harmonic component of the ultrasonic signal which is measured by the input ultrasonic signal measurement section and is incident on the object to be measured.

10. The nonlinear parameter measurement apparatus according to claim 1, wherein the probe has a through-hole, and the through-hole has a central axis coinciding with a beam axis of the ultrasonic signal.

11. An ultrasonic probe for measuring a nonlinear parameter of an object to be measured using an ultrasonic signal, wherein one end of the probe is connected to the object to be measured such that the ultrasonic signal is incident on the object to be measured and the probe has a through-hole therein such that a laser incident on the other end of the probe passes through the through-hole.

12. The ultrasonic probe according to claim 11, wherein the through-hole has a central axis coinciding with a beam axis of the ultrasonic signal.

13. A nonlinear parameter measurement method for measuring a nonlinear parameter of an object to be measured using an ultrasonic signal, the nonlinear parameter measurement method comprising:
  (a) generating an ultrasonic signal by generation of a tone-bust;
  (b) inputting the ultrasonic signal to an ultrasonic buffer section connected to one side of the object to be measured;
  (c) measuring the ultrasonic signal incident on the object to be measured by irradiating the ultrasonic buffer section with a laser;
  (d) measuring an ultrasonic signal output from the object to be measured by irradiating the other side of the object to be measured with the laser; and
  (e) calculating the nonlinear parameter of the object to be measured, based on the measured ultrasonic signal incident on the object to be measured and the measured ultrasonic signal output from the object to be measured.

14. The nonlinear parameter measurement method according to claim 13, wherein the ultrasonic signal incident on the object to be measured is incident as a plane wave.

15. The nonlinear parameter measurement method according to claim 13, wherein the ultrasonic signal and the laser are vertically incident on an incident surface of the object to be measured.

16. The nonlinear parameter measurement method according to claim 13, wherein the ultrasonic signal incident on the object to be measured comprises a basic frequency component and an incident harmonic component of the ultrasonic signal.

17. The nonlinear parameter measurement method according to claim 13, wherein, in the above (c), the ultrasonic signal incident on the object to be measured is measured by measuring a displacement on a surface of the object to be measured on which the ultrasonic signal is incident by the laser.

18. The nonlinear parameter measurement method according to claim 13, wherein the ultrasonic signal output from the object to be measured comprises a basic frequency component of the ultrasonic signal, a secondary harmonic component relative to the basic frequency component, an incident harmonic component of the ultrasonic signal, and a secondary harmonic component relative to the incident harmonic component.

19. The nonlinear parameter measurement method according to claim 13, wherein, in the above (d), the ultrasonic signal output from the object to be measured is measured by measuring a displacement on a surface of the object to be measured from which the ultrasonic signal is output by the laser.

20. The nonlinear parameter measurement method according to claim 13, wherein, in the above (e), the nonlinear parameter of the object to be measured is calculated with consideration for an incident harmonic component of the ultrasonic signal incident on the object to be measured.

* * * * *